(12) United States Patent
Ullah

(10) Patent No.: US 8,901,304 B1
(45) Date of Patent: Dec. 2, 2014

(54) BENZO[D]IMIDAZOLE DERIVATIVES OF PIPERIDINE AND PIPERAZINE

(71) Applicants: King Fahd University of Petroleum and Minerals, Dhahran (SA); King Abdulaziz City for Science and Technology, Riyadh (SA)

(72) Inventor: Nisar Ullah, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 14/072,441

(22) Filed: Nov. 5, 2013

(51) Int. Cl.
 *C07D 403/04* (2006.01)
 *C07D 211/32* (2006.01)
 *C07D 401/04* (2006.01)

(52) U.S. Cl.
 CPC ............ *C07D 403/04* (2013.01); *C07D 401/04* (2013.01)
 USPC .......................................... 544/370; 546/199

(58) Field of Classification Search
 CPC .................................................... C07D 403/04
 See application file for complete search history.

(56) References Cited

U.S. PATENT DOCUMENTS

| | | | |
|---|---|---|---|
| 6,586,425 | B2 | 7/2003 | Cereda et al. |
| 7,115,644 | B2 | 10/2006 | Barbosa, Jr. et al. |
| 8,067,603 | B2 | 11/2011 | Den Hartog et al. |
| 2011/0015207 | A1 | 1/2011 | Volz et al. |

OTHER PUBLICATIONS

Ullah, N. "Synthesis and dual D2 and 5-HT1A receptor binding affinities of 5-piperidinyl and 5-piperazinyl-1H-benzo[d]imidazol-2(3H)-ones." Journal of Enzyme Inhibition and Medicinal Chemistry. (2014), vol. 29, Issue 2, pp. 281-291.*
Barbero et al., "Copper-Catalyzed Intramolecular N-Arylation of Ureas in Water: A Novel Entry to Benzoimidazolones", Tetrahedron (2008), vol. 64(40-31), pp. 7283-7288.
Beyer et al., "Potassium Hydroxide/Dimethyl Sulfoxide Promoted Intramolecular Cyclization for the Synthesis of Benimidazol-2-ones", Organic Letters (2011), vol. 13(11), pp. 2876-2879.

N. Ullah, "Synthesis of new 1-Aryl-4-(biarylmethylene)piperazine ligands, structurally related to adoprazine (SLV313)", Z Naturforsch (2012) vol. 67b, pp. 75-84.
N. Ullah et al., "Synthesis of new 4-aryl-1-(biarylmethylene)piperidines: Structural analogs of adoprazine (SLV313)", Z Naturforsch (2012) vol. 67b, pp. 253-262.

* cited by examiner

*Primary Examiner* — Andrew D Kosar
*Assistant Examiner* — John S Kenyon
(74) *Attorney, Agent, or Firm* — Richard C. Litman

(57) ABSTRACT

The benzo[d]imidazole derivatives of piperidine and piperazine are 5-piperazinyl and 5-piperadinyl-1H-benzo[d]imidazol-2(3H)-ones that exhibit $D_2$ and $5\text{-HT}_{1A}$ receptor binding affinities, making them suitable for use as the active ingredient of pharmaceuticals for the treatment of schizophrenia. The derivatives have the general formula:

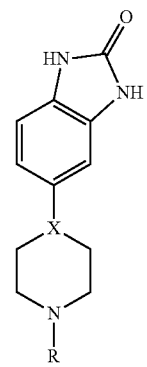

where X is carbon or nitrogen and R is a selected biaryl group, or a pharmaceutically acceptable salt thereof. The piperidinyl compounds are prepared by removal of the Boc group from tert-Butyl-4-(2-oxo-2,3-dihydro-1H-benzo[d]imidazol-5-yl) piperidine-1-carboxylate. Subsequent reductive amination with a selected biarylaldehyde completes the synthesis of the 5-piperazinyl-1H-benzo[d]imidazol-2(3H)-ones. The piperazinyl compounds are prepared by preparation of the intermediate tert-Butyl 4-(3,4-diaminophenyl)piperazine-1-carboxylate. Removal of the Boc group and subsequent reductive amination with a selected biarylaldehyde completes the synthesis of the 5-piperazinyl-1H-benzo[d]imidazol-2(3H)-ones.

14 Claims, 5 Drawing Sheets

BENZO[D]IMIDAZOLE DERIVATIVES OF PIPERIDINE AND PIPERAZINE

BACKGROUND OF THE INVENTION

1. Field of the Invention

The present invention relates to pharmaceuticals, and particularly to benzo[d]imidazole derivatives of piperidine and piperazine useful for the treatment of schizophrenia.

2. Description of the Related Art

Schizophrenia is a devastating psychiatric illness afflicting 1% of the population worldwide. The diagnosis of disease is based on diverse and variably expressed symptoms that can be grouped as positive and negative. The positive symptoms include disorganized thought, delusions, and auditory hallucinations while negative symptoms are emotional flattening, poverty of speech and motivational deficits. The first-generation antipsychotics, such as chlorpromazine 1 and haloperidol 2a, are dopamine antagonists and exhibit robust control of positive symptoms, such as hallucinations, agitation and delusions, but fail to control the negative symptoms, for instance, blunted affect, emotional withdrawal and cognitive deficits.

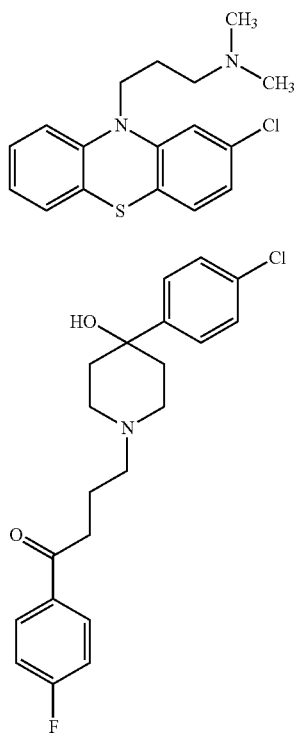

In addition, selective $D_2$ receptor antagonists lead to extrapyramidal symptoms (EPS), such as dystonia and dyskinesia, and hyperprolactinemia. With respect to classical neuroleptics, the 'second-generation' or atypical antipsychotics, such as clozapine 2b, show significantly greater efficacy, including an improved effect on negative symptoms, and causes a marked increase in dopamine output in the prefrontal cortex

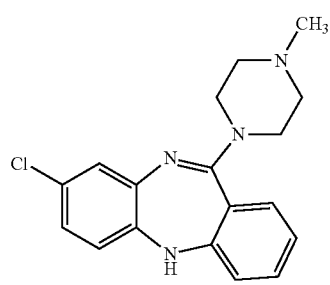

Clozapine 2b exhibits partial agonist efficacy for 5-$HT_{1A}$ receptor-mediated stimulation of G-protein activation, which accounts for part of the activity of clozapine in a model of anxiolytic-like activity, namely, clozapine inhibited stress-induced ultrasonic vocalization in rats, an effect attenuated by selective 5-$HT_{1A}$ antagonist WAY-100635. With respect to first generation antipsychotics, clozapine 2b shows significantly greater efficacy, including an improved effect on negative symptoms, and causes a marked increase in dopamine output in the prefrontal cortex. However, clozapine is implicated in a set of serious side effects, such as weight gain, diabetes and an increased risk of seizures and agranulocytosis.

Although the utility of 5-$HT_{1A}$ receptor agonism in the treatment of schizophrenia is clearly evident, the optimal level of activation of this target is debatable. To achieve improved overall therapeutic benefit, combining $D_2$ receptor antagonism with 5-$HT_{1A}$ receptor agonism, rather than antagonism, has attracted a great deal of interest recently. Several mechanistic considerations and preclinical evidence have supported the potential of such a combination. As a result, adoprazine 3 (SLV-313) and bifeprunox 4, which are potent $D_2$ receptor antagonists and 5-$HT_{1A}$ receptor agonists, were developed.

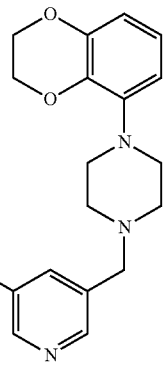

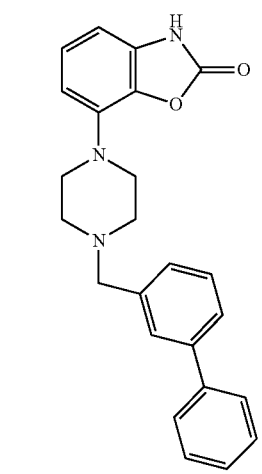

The antipsychotic efficacy of bifeprunox 4 was determined to be inferior to that of risperidone and olanzapine, and despite a satisfactory tolerance profile, the FDA did not grant marketing approval. The lack of sufficient antipsychotic efficacy of bifeprunox 4 likely reflects its marked agonism at $D_2$ receptors. Thus, bifeprunox 4 suppresses basal firing rates of dopaminergic neurons in the ventral tegmental area and elicits circling behavior in rats unilaterally lesioned with 6-OH-DA. In addition, the failure of adoprazine 3 and bifeprunox 4 to oppose phencyclidine-induced social interaction deficits suggested that an appropriate 'balance' of activity at these sites is necessary for activity in this model. Therefore, there is a need to discover new chemical entities bearing varying ratios of $D_2$ and $5\text{-HT}_{1A}$ activities.

Thus, benzo[d]imidazole derivatives of piperidine and piperazine solving the aforementioned problems are desired.

SUMMARY OF THE INVENTION

The benzo[d]imidazole derivatives of piperidine and piperazine are 5-piperazinyl and 5-piperadinyl-1H-benzo[d]imidazol-2(3H)-ones that exhibit $D_2$ and $5\text{-HT}_{1A}$ receptor binding affinities, making them suitable for use as the active ingredient of pharmaceuticals for the treatment of schizophrenia. The derivatives have the general formula:

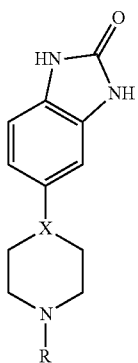

where X is carbon or nitrogen and R is a group selected from a through f having the formula:

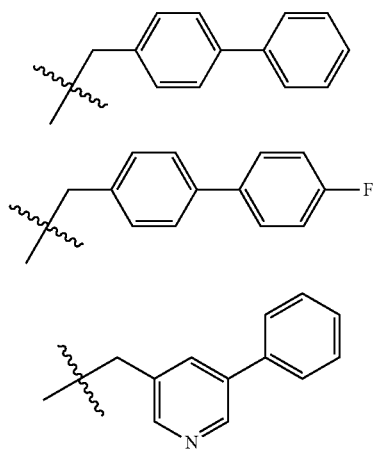

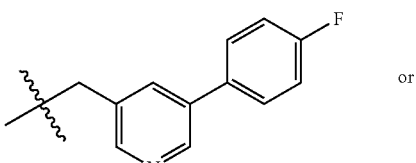

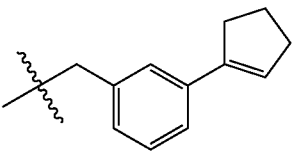

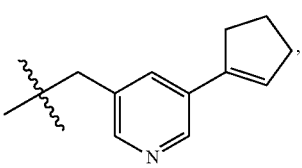

or a pharmaceutically acceptable salt thereof. The piperidinyl compounds are prepared by removal of the Boc group from tert-Butyl-4-(2-oxo-2,3-dihydro-1H-benzo[d]imidazol-5-yl)piperidine-1-carboxylate. Subsequent reductive amination with the biarylaldehydes a through f completes the synthesis of the 5-piperazinyl-1H-benzo[d]imidazol-2(3H)-ones. The piperazinyl compounds are prepared by preparation of the intermediate tert-Butyl 4-(3,4-diaminophenyl)piperazine-1-carboxylate. Removal of the Boc group and subsequent reductive amination with the biarylaldehydes a through f completes the synthesis of the 5-piperazinyl-1H-benzo[d]imidazol-2(3H)-ones.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The benzo[d]imidazole derivatives of piperidine and piperazine are 5-piperazinyl and 5-piperadinyl-1H-benzo[d]imidazol-2(3H)-ones that exhibit $D_2$ and $5-HT_{1A}$ receptor binding affinities, making them suitable for use as the active ingredient of pharmaceuticals for the treatment of schizophrenia. The derivatives have the general formula:

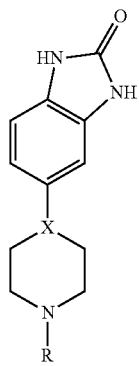

where X is carbon or nitrogen and R is a group selected from a through f having the formula:

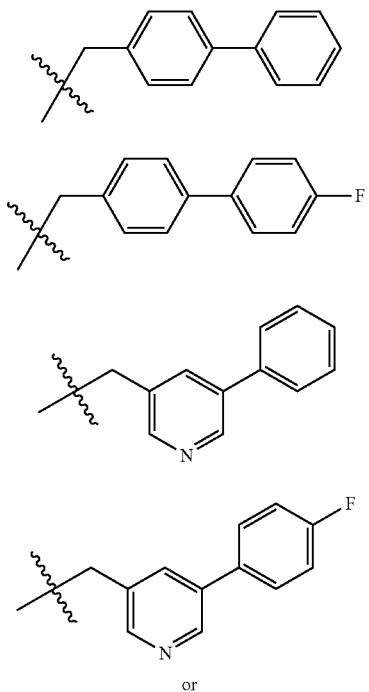

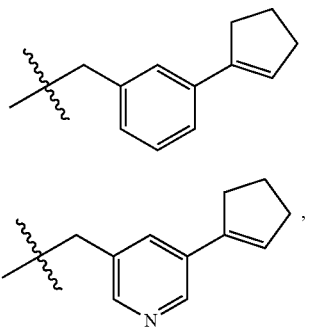

or a pharmaceutically acceptable salt thereof. The piperidinyl compounds are prepared by removal of the Boc group from tert-Butyl-4-(2-oxo-2,3-dihydro-1H-benzo[d]imidazol-5-yl)piperidine-1-carboxylate. Subsequent reductive amination with the biarylaldehydes a through f completes the synthesis of the 5-piperazinyl-1H-benzo[d]imidazol-2(3I)-ones. The piperazinyl compounds are prepared by preparation of the intermediate tert-Butyl 4-(3,4-diaminophenyl)piperazine-1-carboxylate. Removal of the Boc group and subsequent reductive amination with the biarylaldehydes a through f completes the synthesis of the 5-piperazinyl-1H-benzo[d]imidazol-2(3H)-ones.

Figure 1:
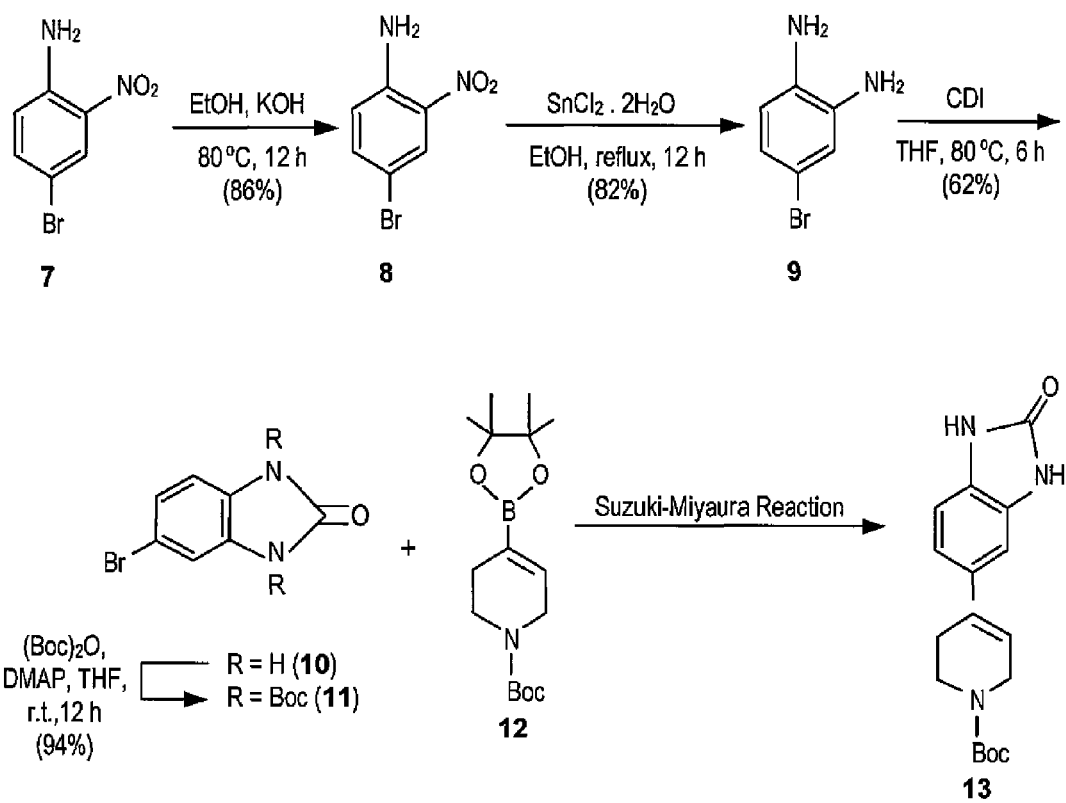
FIG. 1 is a proposed reaction scheme for the synthesis of an intermediate compound, namely, tert-Butyl 4-(3,4-diaminophenyl)piperidine-1-carboxylate, which is used in the synthesis of the benzo[d]imidazole derivatives of piperidine according to the present invention.

The synthesis of the benzo[d]imidazole derivatives of piperidine required the synthesis of intermediate 5, which was to be synthesized from 13. As shown in FIG. 1, the synthesis of the latter was envisioned by Suzuki-Miyaura reaction of bromo-1H-benzo[d]imidazol-2(3H)-one 10 with boronate 12. Preparation of 10 was commenced by the basic hydrolysis of acetamide 7 to produce nitroaniline 8, which, in turn, was transformed to benzenediamine 9 by the action of stannous chloride. Reaction of 9 with carbonyldiimidazole (CDI) finally produced 10 in 62% yield. Suzuki-Miyaura reaction of cyclic vinyl boronate 12, which was derived from the vinyl trifluorates of N-protected tetrahydropyridines, with 10 under a variety of conditions (such as $PdCl_2dppf$, KOAc, DMF, 80° C.; $Pd(PPh_3)_4$, toluene, ethanol, $Na_2CO_3$, reflux) unexpectedly failed. The desired 13 could not be obtained. Rather, the starting compound 10 was recovered. The poor solubility of compound 10 in a variety of solvents is considered to be one of the factors for its lack of reactivity. Thus, intermediate 10 was protected with di-tert-butyl dicarbonate to furnish compound II, which, in turn, was employed in Suzuki-Miyaura reaction with boronate 12, under different conditions as described in the case of compound 10. However, the desired product 13 was not detected.

Figure 2:
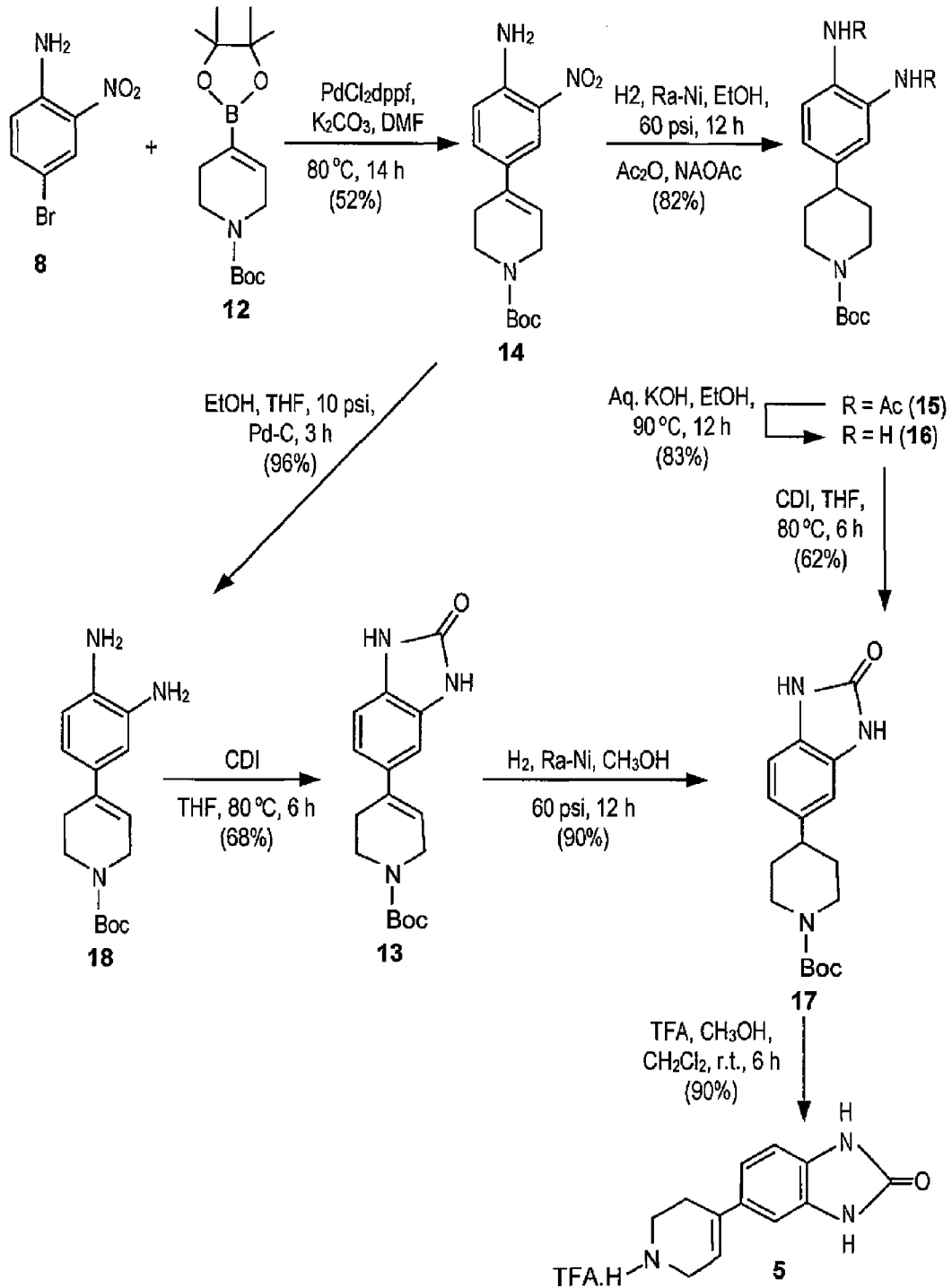
FIG. 2 is an alternative reaction scheme for the synthesis of the intermediate compound, tert-Butyl 4-(3,4-diaminophenyl)piperidine-1-carboxylate, as well as 5-(Piperidin-4-yl)-1H-benzo[d]imidazol-2(3H)-one, which are used in the synthesis of the benzo[d]imidazole derivatives of piperidine according to the present invention.

As shown in FIG. 2, in an alternate approach, boronate 12 was reacted with nitroamine 8 under Suzuki-Miyaura conditions to produce intermediate 14, which, in turn, was subjected to hydrogenation in a Parr apparatus at 60 psi. The hydrogenation required an extended period of time (20 hours) and was unclean, yielding the desired diamine 15 in a very low yield (20%) after column purifications. Thus, hydrogenation of compound 14 was performed in ethanol in the presence of acetic anhydride (6 equivalents) and sodium acetate (4 equivalents), which rendered reduction of both the nitro group and a double bond with concomitant acetylation of the amino groups, yielding intermediate 15 in 82% yield. Basic hydrolysis of the latter with aqueous KOH in ethanol ultimately generated diamine 16 in good yield (83%). Reaction of 16 with CDI in THF, heating the mixture at 80° C. for 6 hours, finally gave access to the key intermediate 17 in an overall yield of 42% from compound 14. Alternatively, intermediate 17 was also synthesized from 14 by hydrogenation of 14 over Pd—C at 10 psi to produce diamine 18, which was treated with CDI in THF to generate intermediate 13. Hydrogenation of the latter over Ra—Ni in methanol furnished intermediate 17 in an overall higher yield of 59% from 14. This approach did not require column purifications of intermediates (13 and 17), as was the case with intermediates 15 and 16. Exposure of intermediate 17 to trifluoroacetic acid in a mixture of methanol and dichloromethane finally furnished the desired key intermediate 5.

Figure 3:
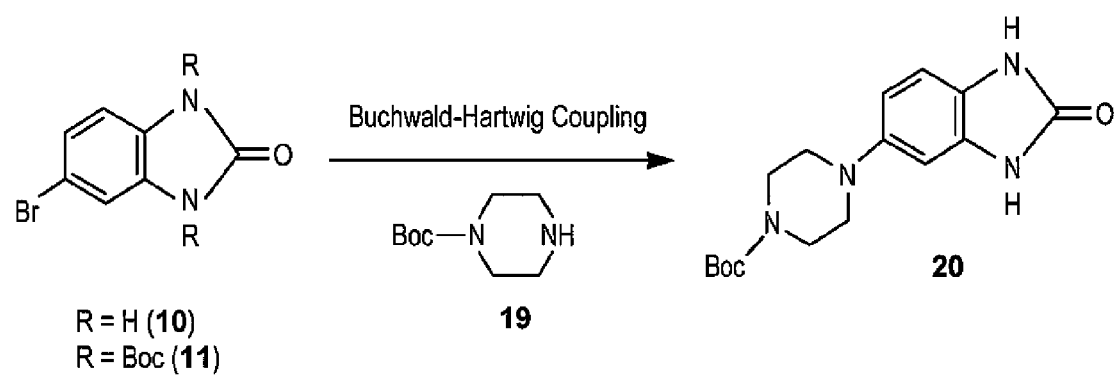
FIG. 3 is a proposed reaction scheme for the synthesis of an intermediate compound, namely, tert-Butyl 4-(2-oxo-2,3-dihydro-1H-benzo[d]imidazol-5-yl)piperazine-1-carboxylate, which is used in the synthesis of the benzo[d]imidazole derivatives of piperazine according to the present invention.

The synthesis of the benzo[d]imidazole derivatives of piperazine required the synthesis of intermediate 6, which was to be accomplished from intermediate 20. The Buchwald-Hartwig coupling of bromides 10 or 11 with tert-butyl piperazine-1-carboxylate 19, shown in FIG. 3, under different reaction conditions ($PdCl_2dppf$, KOAc, DMF, 80° C.; $Pd(PPh_3)_4$, toluene, ethanol, $Na_2CO_3$, reflux) were not successful. The desired intermediate 20 was not observed in any case.

Figure 4:
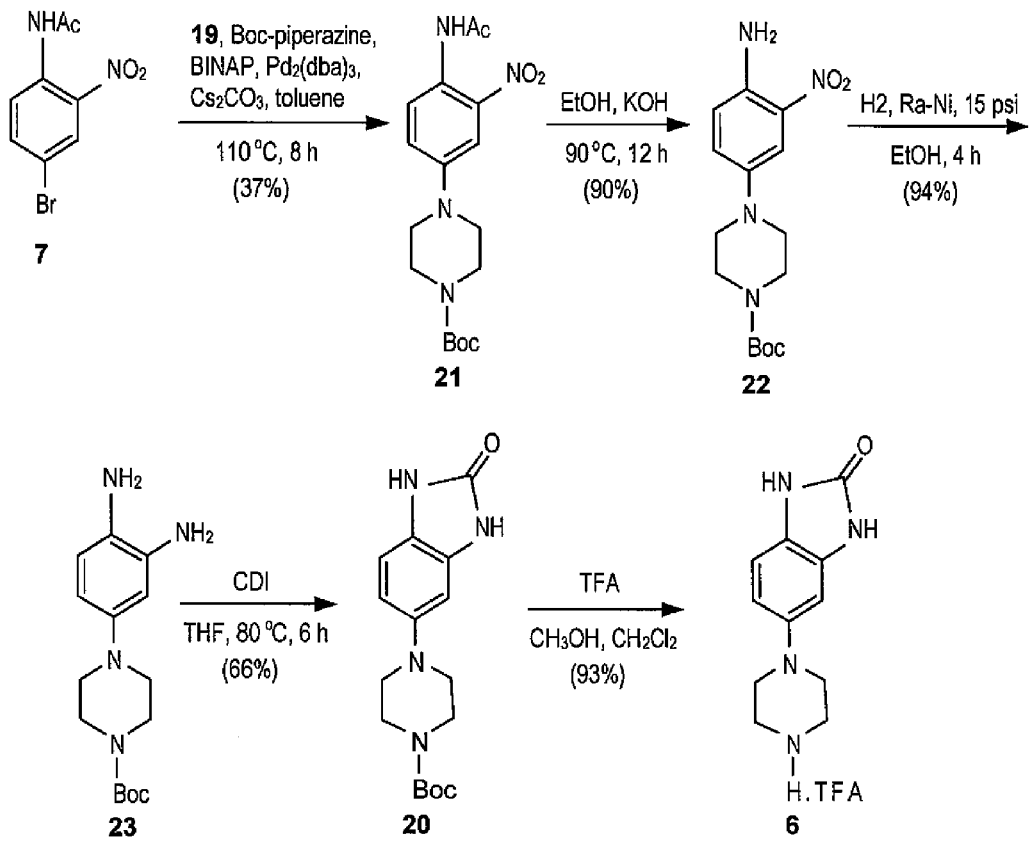
FIG. 4 is a reaction scheme for the synthesis of an intermediate compound, namely, 5-(piperazin-1-yl)-1H-benzo[d]imidazol-2(3H)-one, which is used in the synthesis of the benzo[d]imidazole derivatives of piperazine according to the present invention.
Figure 5:
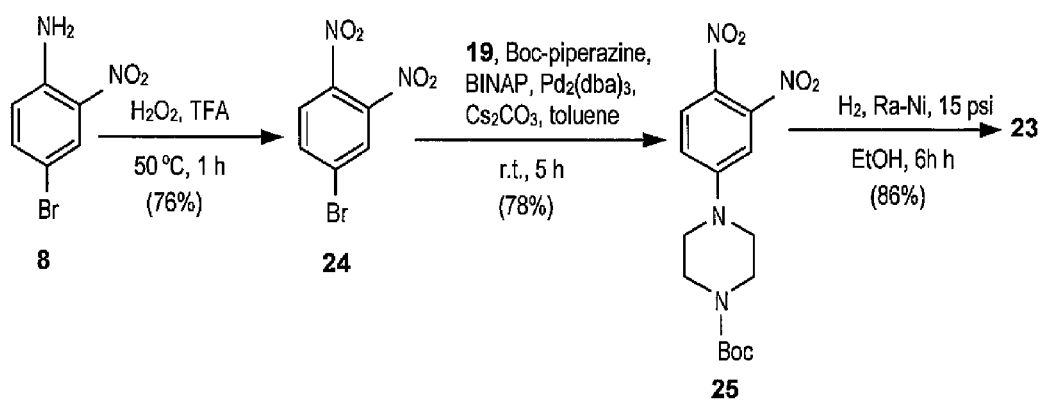
FIG. 5 is a reaction scheme for the synthesis of an intermediate compound, namely, tert-Butyl 4-(3,4-diaminophenyl)piperazine-1-carboxylate, which is used in the synthesis of the benzo[d]imidazole derivatives of piperazine according to the present invention.

In an alternate approach, shown in FIG. 4, acetamide 7 was coupled with compound 19 under Buchwald-Hartwig reaction conditions to construct the adduct 21 in relatively low yield (37%). Hydrolysis of the latter with aqueous KOH gave nitroaniline 22, which, in turn, was subjected to hydrogenation in a Parr apparatus over Ra—Ni at 15 psi to produce diamine 23 in an overall yield of 31% from compound 7. Alternatively, as shown in FIG. 5, intermediate 23 was also synthesized from oxidation of compound 8 with trifluoroperacetic acid, generated in situ from hydrogen peroxide and trifluoroacetic acid, to produce dinitrobenzene 24, which was coupled with compound 19 under Buchwald-Hartwig reaction conditions at room temperature to produce adduct 25. Hydrogenation of intermediate 25, as described for the preparation of compound 23 from compound 22, finally produced compound 23 in an overall yield of 51% from compound 8. It is worth mentioning that reaction of compound 24 with compound 19 without the addition of catalyst at room temperature did not progress. The starting materials were intact or degraded over the course of longer reaction time, whereas gentle heating of the reaction mixture to 40° C. resulted in a complex mixture of side products. The desired compound 19 was not observed. This was attributed to thermal instability of compound 24, since gentle heating of the reaction mixture under Buchwald-Hartwig reaction conditions did not yield the desired compound 19 either. Only side products were observed. Reaction of compound 23 with CDI in THF at 80° C. yielded the desired intermediate 20, which was exposed to acid to produce the key intermediate 6 in 93% yield.

Figure 6:
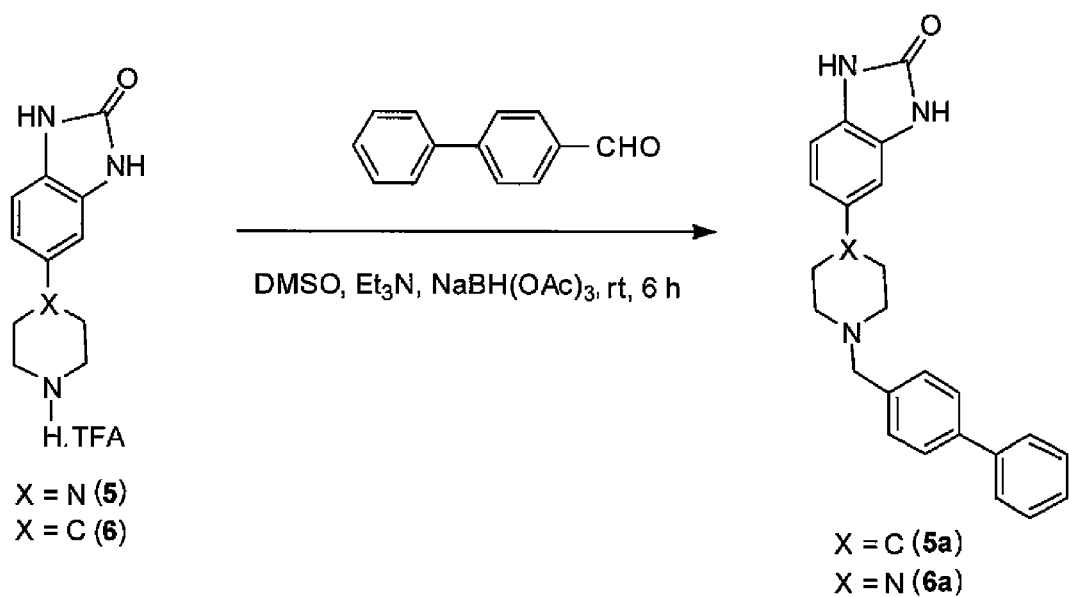
FIG. 6 is a reaction scheme for the synthesis of the benzo[d]imidazole derivatives of piperidine and piperazine according to the present invention.

Having the desired intermediates 5 and 6 in hands, as shown in FIG. 6, we next performed reductive amination of 5 and 6 with aldehydes a through f in DMSO, using $NaBH(OAc)_3$ as reducing agent to accomplish the synthesis of final compounds 5a through 5f and 6a through f, respectively.

Details of the synthesis of the various compounds shown in FIGS. 1-6 are described in the following examples. Melting Points were determined on a Btichi apparatus (Btichi Labortechnik AG, Switzerland) and are uncorrected. Elemental analysis was carried out on a Perkin Elmer Elemental Analyzer Series 11 Model 2400 (PerkinElmer Inc. USA). IR spectra were recorded on a Perkin Elmer 16F PC FTIR spectrophotometer (PerkinElmer Inc. USA). The $^1$I-I and $^{13}$C NMR spectra were measured in CDC13 and d6-DMSO using TMS as internal standard on a JEOL JNMLA 500 MHz spectrometer (JEOL USA Inc.). Mass spectra were recorded on Agilent Technologies 6890N GC-MS system (Agilent Technologies Inc. USA). Analytical TLC was carried out on silica gel 60 F254 plates (E. Merck). Column chromatography was carried out on silica gel (200-400 mesh, E. Merck).

Example 1

Synthesis of di-tert-Butyl 5-bromo-2-oxo-1H-benzo[d]imidazole-1,3(2H)-dicarboxylate 11

To a solution of compound 10 (0.4 g, 1.88 mmol) in anhydrous THF (15 mL) was added di-tert-butyl dicarbonate (1.64 g, 7.52 mmol) followed by the addition of 4-dimethylaminopyridine (0.23 g, 1.88 mmol), and the mixture was stirred overnight at room temperature. The mixture was diluted with ethyl acetate (25 mL) and washed successively with water (15 mL) and brine (15 mL), and then dried over $Na_2SO_4$ and evaporated. Column chromatography on silica gel, eluting with ethyl acetate:hexanes (10:90) and then changing to (20:80) gave the title compound II. Yield: 94%, colorless amorphous solid, mp 109-110° C. IR (KBr, $cm^1$) 3041 (Ar—H), 2978 (Alph-H), 1691 (C=0), 1612, 1442 (C=C), 1222 (C—N), 1175 (C-0); $^1$HNMR (500 MHz, $CDCl_3$) δ 1.63 (s, 18H, $OC(CH_3)_3$), 7.33 (dd, J=2.3, 8.4 Hz, 1H, H-6), 7.74 (d, J=8.4 Hz, 11-1, H-7), 8.08 (d, J=2.4 Hz, 1H, H-4), $^{13}$C NMR (125.7 MHz, $CDCl_3$) δ 27.76 ($OC(CH_3)_3$), 85.66 ($OC(CH_3)_3$), 115.26 (C-4), 117.26 (C-7), 125.15 (C-5), 127.08 (C-6), 146.73 (C-8), 148.17 (C-3), 154.68 (CO), 155.46 (CO). Anal. Calcd for $C_{17}H_{21}BrN_2O_5$: C, 49.41; H, 5.12; N, 6.78%. Found: C, 49.35; H, 5.17; N, 6.68%.

Example 2

Synthesis of tert-Butyl 4-(4-amino-3-nitrophenyl)-5,6-dihydropyridine-1(2H)-carboxylate 14

To a nitrogen-flushed flask containing the boronate 12 (1.39 g, 4.5 mmol), $K_2CO_3$ (1.86 g, 13.5 mmol) and $PdCl_2dppf$ (0.23 g, 0.28 mmol) was added a solution of the bromide 8 (1.03 g, 4.74 mmol) in DMF (30 mL). The mixture was heated to 80° C. and stirred under $N_2$ overnight when TLC indicated completion of the reaction. The reaction was cooled to room temperature and filtered through a pad of celite. The filtrate was added to ethyl acetate (50 mL) and washed successively with water (20 mL) and brine (3×15 mL), then dried over $Na_2SO_4$ and evaporated. Column chromatography of the brown oily material on silica gel, eluting with ethyl acetate:hexanes (30:70) and then changing to (50:50) gave compound 14. Yield: 52%, light yellow amorphous solid, mp 111-112° C. IR (KBr, $cm^I$) 3420, 3310 ($NH_2$), 3030 (Ar—H), 2979 (Alph-H), 1690 (CO), 1612, 1515, 1414 (C—C), 1254 (C—N), 1159 (C-0); $^1$H NMR (500 MHz, $CDCl_3$) δ1.45 (s, 9H, $OC(CH_3)_3$), 2.44 (br. s, 2H, $CH_2$), 3.59 (m, 2H, $CH_2$), 4.08 (br. s, 2H, $CH_2$), 5.95 (br. s, 1H, CH), 6.20 (br. s, 2H, $NH_2$), 6.76 (d, J=8.8 Hz, 1H, H-5), 7.41 (dd, J=2.8, 8.8 Hz, 1H, H-6), 8.02 (br. s, 1H, H-2). $^{13}$C NMR (125.7 MHz, $CDCl_3$) δ 26.88 ($CH_2$), 28.39 ($OC(CH_3)_3$), 29.36 ($CH_2$), 42.86 ($CH_2$), 79.99 ($OC(CH_3)_3$), 118.87 (CH), 119.14 (C-5), 121.47 (C-2), 129.49 (C-1), 131.65 (C-3), 132.36 (C-6), 143.89 (C-4), 154.73 (CO). Anal Calcd for $C_{16}H_{21}N_3O_4$: C, 60.17; H, 6.63; N, 13.16%. Found: C, 60.10; H, 6.68; N, 13.08%.

Example 3

Synthesis of tert-Butyl 4-(3,4-diacetamidophenylOpiperidine-1-carboxylate 15

To a solution of compound 14 (1.4 g, 4.39 mmol), acetic anyhydride (2.48 mL, 26.28 mmol), and sodium acetate (1.44 g, 17.52 mmol) in a mixture of THF (10 mL) and EtOH (20 mL) was added Ra—Ni (20% w/w) and the mixture was subjected to hydrogenation in a Parr apparatus at 60 psi for 8 hours. After filtering over the pad of celite, the solution was concentrated to get a brown oil material, which was resolved over silica column, eluting with ethyl acetate:hexanes (30:70) and then changing to (60:40) to get 15. Yield: 82%, light brown gum. IR (KBr, cm$^{-1}$) 3420, 3338 (NH$_2$), 3033 (Ar—H), 2978 (Alph-H), 1691 (CO), 1620, 1524, 1408 (C=C), 1221 (C—N), 1154 (C-0); $^1$H NMR (500 MHz, CDCl$_3$) δ 1.47 (s, 91-1, OC(CH$_3$)$_3$), 1.71 (m, 2H, CH$_2$), 2.03 (s, 31-1, COCH$_3$), 2.09 (s, 3H, COCH$_3$), 2.57 (m, 1H, CH), 2.75 (br. s, 2H, CH$_2$), 3.41 (br. s, 2H, CH$_2$), 4.19 (br. s, 2H, CH$_2$), 6.96 (dd, J=2.4, 8.2 Hz, 11-1, H-6), 7.18 (d, J=2.3 Hz, 1H, H-2), 7.29 (d, J—8.2 Hz, 1H, H-5), 8.80 (s, 1H, NH), 8.86 (s, 1H, NH). $^{13}$C NMR (125.7 MHz, CDCl$_3$) δ 23.81 (COCH3), 24.83 (COCH3), 24.93 (CH$_2$), 28.51 (OC(CH$_3$)$_3$), 33.04 (CH), 42.06 (CH$_2$), 79.77 (OC(CH$_3$)$_3$), 123.51 (C-2/C-5), 124.49 (C-2/C-5), 125.60 (C-6), 128.70 (C-4), 130.66 (C-3), 143.82 (C-1), 154.91 (CO), 170.08 (CO). Anal. Calcd for C$_{20}$H$_{29}$N$_3$O$_4$: C, 63.98; H, 7.79; N, 11.19%. Found: C, 63.90; H, 7.85; N, 11.10%.

Example 4

Synthesis of tert-Butyl 4-(3,4-diaminophenyl)piperidine-1-carboxylate 16

To a solution of compound 15 (0.75 g, 2 mmol) in ethanol (20 mL) was added 4M solution of KOH in H$_2$O (4 mL, 16 mmol), and the mixture was stirred at 90° C. for 12 h. The mixture was concentrated under reduced pressure to get a brown oil material, which was resolved over silica column, eluting with ethyl acetate:hexanes (50:50) and then changing to (90:10) to get compound 16. Yield: 83%, dark brown gum. IR (KBr, cm$^{-1}$) 3420, 3338 (NH$_2$), 3033 (Ar—H), 2978 (Alph-H), 1691 (CO), 1620, 1524, 1408 (C=C), 1221 (C—N), 1154 (C-0); $^1$H NMR (500 MHz, CDCl$_3$) δ 1.49 (s, 9H, OC(CH$_3$)$_3$), 1.81 (m, 2H, CH$_2$), 2.07 (m, 2H, CH$_2$), 2.72-2.82 (m, 5H, CH, CH$_2$), 4.24 (br. s, 4H, 2NH$_2$), 7.04 (dd, J=2.5, 8.5 Hz, 1H, H-6), 7.32 (d, J=2.4 Hz, 1H, H-2), 7.45 (d, J=8.5 Hz, 1H, H-5). $^{13}$C NMR (125.7 MHz, CDCl$_3$) δ 28.40 (OC(CH$_3$)$_3$), (CH), 29.95 (CH$_2$), 33.72 (CH), 42.78 (CH$_2$), 79.52 (OC(CH$_3$)$_3$), 123.50 (C-2/C-5), 123.66 (C-2/C-5), 126.60 (C-6), 127.43 (C-4), 140.29 (C-3), 154.96 (CO). Anal. Calcd for C$_{16}$H$_{25}$N$_3$O$_2$: C, 65.95; H, 8.65; N, 14.42%. Found: C, 65.87; H, 8.70; N, 14.33%.

Example 5

Synthesis of tert-Butyl 4-(3,4-diaminophenyl)-5,6-dihydropyridine-1(2H)-carboxylate 18

To a solution of compound 14 (2.1 g, 6.58 mmol) in a mixture of THF (15 mL) and EtOH (30 mL) was added Pd—C (0.21 g, 10% wet basis), and the mixture was subjected to hydrogenation in a Parr apparatus at 10 psi for 3 hours. After filtering over the pad of celite, the solution was concentrated and loaded over a silica column, eluting with ethyl acetate:hexanes (50:50), and then changing to (90:10) to get compound 18. Yield 96%, light brown gum. IR KBr, cm$^{-1}$) 3429, 3330 (NH$_2$), 3036 (Ar—H), 2983 (Alph-H), 1691 (CO), 1628, 1520, 1415 (C=C), 1229 (C—N), 1160 (CO); $^1$H NMR (500 MHz, CDCl$_3$) δ 1.46 (s, 91-1, OC(CH$_3$)$_3$), 2.40 (br. s, 2H, CH$_2$), 3.43 (m, 2H, CH$_2$), 4.02 (br. s, 2H, CH$_2$), 4.38 (br. s, 4H, 2NH$_2$), 5.93 (br. s, 1H, CH), 7.06 (dd, J=2.6, 8.2 Hz, 1H, H-6), 730 (d, J=2.5 Hz, 1H, H-2), 7.46 (d, J=8.2 Hz, 1H, H-5). $^{13}$C NMR (125.7 MHz, CDCl$_3$) δ 26.89 (CH$_2$), 28.33 (OC(CH$_3$)$_3$), 29.39 (CH$_2$), 42.84 (CH$_2$), 79.99 (OC(CH$_3$)$_3$), 118.77 (CH), 119.19 (C-5), 120.37 (C-2), 129.19 (C-1), 130.65 (C-3), 131.16 (C-6), 141.82 (C4), 154.63 (CO). Anal. Calcd for C$_{16}$H$_{23}$N$_3$O$_2$. C, 66.41; H, 8.01; N, 14.52%. Found: C, 66.33; H, 8.07; N, 14.43%.

Example 6

Synthesis of tert-Butyl 4-(2-oxo-2,3-dihydro-1H-benzo[d]imidazol-5-yl)-5,6-dihydropyridine-1(2H)-carboxylate 13

A mixture of compound 18 (0.58 g, 2 mmol) and CDI (0.34 g, 2.1 mmol) in THF (10 mL) was stirred at 60° C. for 6 h. The solvent was removed in vacuo, the residue was triturated with diethyl ether, and the resultant off-white solid was filtered and washed with diethyl ether to obtain compound 13. Yield: 68%, off-white solid, mp 244-245° C. IR (KBr, cm$^1$) 3433, 3191 (CONH), 3037 (Ar—H), 2978 (Alph-H), 1713, 1689 (C=0), 1604, 1433 (C=C), 1244 (C—N), 1178 (C-0); $^1$H NMR (500 MHz, DMSO d6)$_g$ 1.39 (s, 9H, OC(CH$_3$)$_3$), 2.48 (br. s, 2H, CH$_2$), 3.54 (m, 2H, CH$_2$), 3.93 (br. s, 2H, CH$_2$), 5.97 (br. s, 1H, CH), 6.86 (d, J=8.2 Hz, 1H, H-7), 6.95 (d, J=2.4 Hz, 1H, H-4), 6.99 (dd, J=2.4, 8.2 Hz, 1H, H-6), 10.60 (br. s, 2FI, NH). $^{13}$C NMR (125.7 MHz, DMSO d6) δ 26.84 (CH$_2$), 28.28 (OC(CH$_3$)$_3$), 32.33 (CH), 42.80 (CH$_2$), 79.08 (OC(CH$_3$)$_3$), 105.16 (CH), 108.52 (C-4), 117.67 (C-7), 129.20 (C-6), 130.04 (C-8), 133.28 (C-5/C-9), 134.81 (C-5/C-9), 154.73 (CO), 155.67 (CO). Anal. Calcd for C$_{17}$H$_{21}$N$_3$O$_3$: C, 64.74; H, 6.71; N, 13.32%. Found: C, 64.68; H, 6.76; N, 13.24%.

Example 7 tert-Butyl 4-(2-oxo-2,3-dihydro-1H-benzo[d]imidazol-5-yl)piperidine-1-carboxylate 17

For synthesis from compound 16, following the same procedure adopted for the synthesis of 13, the title compound 17 was obtained from the reaction of compound 16 with CDI. Yield: 62%, off-white solid. For synthesis from compound 13, to a solution of compound 13 (0.94 g, 3 mmol) in CH$_3$OH (30 mL) was added Ra—Ni (0.20 g, 10% wet basis), and the mixture was subjected to hydrogenation in a Parr apparatus at 60 psi for 12 hours. After filtering over the pad of celite, the solution was concentrated and recrystallized from diethyl ether to get compound 17. Yield: 90%, off-white solid, mp>250° C. IR (KBr, cm$^1$) 3290, 3175 (CONH), 3030 (Ar—H), 2989 (Alph-H), 1691 (CO), 1613, 1515, 1416 (C=C), 1220 (C—N), 1167 (C-0); $^1$H NMR (500 MHz, DMSO d6) δ 1.38 (s, 9H, OC(CH$_3$)$_3$), 1.86 (m, al, CH$_2$), 2.06 (m, 211, CH$_2$), 2.40-2.48 (m, 3H, CH, CH$_2$), 3.44 (obscured by H$_2$O, 2H, CH$_2$), 6.70-6.80 (m, 3H, H-4, H-6, H-7), 10.49 (br. s, 1H, NH), 10.53 (br. s, 1H, NH). $^{13}$C NMR (125.7 MHz, DMSO d6) δ 28.15 (OC(CH$_3$)$_3$), 29.25 (CH$_2$), 33.24 (CH$_2$), 41.72 (CH$_2$), 78.72 (OC(CH$_3$)$_3$), 106.93 (C-4), 108.48 (C-7), 119.0 (C-6), 128.09 (C-8), 129.89 (C-9), 138.49 (C-5), 154.05 (CO), 155.61 (CO). Anal. Calcd for C$_{17}$H$_{23}$N$_3$O$_3$: C, 64.33; H, 7.30; N, 13.24%. Found: C, 64.25; H, 7.35; N, 13.15%.

Example 8

Synthesis of 5-(Piperidin-4-yl)-1H-benzo[d]imidazol-2(3H)-one 5

To a solution of compound 17 (0.95 g, 3 mmol) in a mixture of CH$_2$Cl$_2$ (15 mL) and CH$_3$OH (20 mL) was added trifluoroacetic acid (3 mL) at 0° C., and the mixture was stirred for 6 h at room temperature. Solvents were evaporated under reduced pressure, and triturating with diethyl ether gave the title compound 5. Yield: 90%, light yellow solid, mp 214-215° C. IR (KBr, cm$^{-1}$) 3238 (CONH), 3043 (Ar—H), 2956 (Alph-H), 1692 (CO), 1612, 1446 (C—C), 1180 (C—N), 1126 (C-0); $^1$HNMR (500 MHz, DMSO d6) δ 1.73-188 (m, 3H, CH, CH$_2$), 2.77 (m, 2H, CH$_2$), 2.97 (m, 2H, CH$_2$), 3.44 (obscured by H$_2$O, 2H, CH$_2$), 4.46 (m, 1H, CH), 6.74-6.84 (m, 3H, H-4, H-6, H-7), 10.50 (br. s, 1H, NH), 10.54 (br. s, 1H, NH). $^{13}$C NMR (125.7 MHz, DMSO d6) δ 30.04 (CH$_2$), 33.37 (CH), 43.86 (CH$_2$), 106.66 (C-4), 118.43 (C-7), 118.94 (C-6), 128.37 (C-8), 129.87 (C-9), 137.24 (C-5), 155.56 (CO). Anal. Calcd for C$_{14}$H$_{16}$F$_3$N$_3$O$_3$: C, 50.76; H, 4.87; N, 12.68%. Found: C, 50.70; H, 4.92; N, 12.60%.

Example 9 tert-Butyl 4-(4-acetamido-3-nitrophenyl)piperazine-1-carboxylate 21

To an oven-dried flask, 1-boc-piperazine (3.19 g, 17.1 mmol), Cs$_2$CO$_3$ (5.82 g, 17.86 mmol), Pd$_2$(dba)$_3$ (1.44 g, 1.57 mmol), rac-2,2'bis(diphenylphosphino)-1,1'-binaphthyl (0.89 g, 1.43 mmol), toluene (8 mL) and compound 7 (3.68 g, 14.26 mmol) were added. While stirring the reaction mixture at room temperature, the air in the flask was removed and replaced by N$_2$. This process was repeated three times. The reaction temperature was brought to 110° C. and stirred for 8 h. Ethyl acetate (40 mL) was added to the mixture at room temperature, washed with H$_2$O (15 mL) and brine (10 mL), dried over Na$_2$SO$_4$ and evaporated. The brown oily material was chromatographed on a silica column, eluting with hexanes:ethyl acetate (3:7), and then changing to (1:1) to obtain compound 18. Yield: 37%, light red solid. IR (KBr, cm$^{-1}$) 3310, 3168 (NH), 3176 (Ar—H), 1709, 1678 (CO), 1519, 1416 (C—C), 1210 (C—N), 1151 (C—O); $^1$H NMR (500 MHz, CDCl$_3$) δ 1.49 (s, 9H, OC(CH$_3$)$_3$), 2.17 (s, 3H, COCH$_3$), 3.15 (m, 4H, 2CH$_2$), 3.60 (m, 4H, 2CH$_2$), 7.22 (dd, J=2.5, 8.5 Hz, 1H, H-6), 7.62 (d, J=2.5 Hz, 1H, H-2), 7.57 (d, J=8.5 Hz, 1H, H-5), 9.98 (br. s, 1H, NH). $^{13}$C NMR (125.7 MHz, CDCl$_3$) δ 25.59 (COCH$_3$), 28.40 (OC(CH$_3$)$_3$), 48.92 (CH$_2$), 52.31 (CH$_2$), 79.94 (OC(CH$_3$)$_3$), 111.29 (C-2), 123.52 (C-5/C-6), 124.31 (C-5/C-6), 127.45 (C4), 137.45 (C-3), 147.11 (C-1), 154.63 (CO), 168.78 (CO). Anal. Calcd for C$_{17}$H$_{24}$N$_4$O$_5$: C, 56.03; H, 6.64; N, 15.38%. Found: C, 55.96; H, 6.69; N, 15.30%.

Example 10

Synthesis of tert-Butyl 4-(4-amino-3-nitrophenyl)piperazine-1-carboxylate 22

Following the same procedure adopted for the synthesis of 16, the title compound 22 was obtained from the basic hydrolysis of compound 21. Yield: 90%, blood red solid, mp 128-129° C. IR (KBr, cm$^1$) 3477, 3325 (Ar—NH$_2$), 3073 (Ar—H), 1673 (CO), 1516, 1412 (C=C), 1211 (C—N), 1161 (C—O); $^1$H NMR (500 MHz, CDCl$_3$) δ 1.47 (s, 9H, OC(CH$_3$)$_3$), 3.00 (m, 4H, 2CH$_2$), 3.57 (m, 4H, 2CH$_2$), 5.92 (br. s, 2H, NH$_2$), 6.79 (d, J=8.1 Hz, 1H, H-5), 7.15 (m, 1H, H-6), 7.56 (d, J—2.1 Hz, 1H, H-2). $^{13}$C NMR (125.7 MHz, CDCl$_3$) δ 28.42 (OC(CH$_3$)$_3$), 43.21 (CH$_2$), 50.49 (CH$_2$), 79.97 (OC (CH$_3$)$_3$), 111.63 (C-2), 119.85 (C-5), 128.88 (C-6), 131.89 (C-4), 140.00 (C-3), 142.69 (C-1), 154.61 (CO). Anal. Calcd for C$_{15}$H$_{22}$N$_4$O$_4$: C, 55.89; H, 6.88; N, 17.38%. Found: C, 55.81; H, 6.94; N, 17.30%.

Example 11

Synthesis of tert-Butyl 4-(3,4-diaminophenyl)piperazine-1-carboxylate 23

Following the same procedure adopted for the synthesis of 18, the title compound 23 was obtained from compound 22. Yield: 71%, light brown solid, mp 118-119° C. IR (KBr, cm$^1$) 3427, 3336 (NH$_2$), 3030 (Ar—H), 2973 (Alph-H), 1693 (CO), 1623, 1522, 1405 (C=C), 1249 (C—N), 1162 (C-0); NMR (500 MHz, DMSO d6) δ 1.37 (s, 9H, OC(CH$_3$)$_3$), 2.77 (br. s, 4H, 2CH$_2$), 3.37 (br. s, 4H, 2CH$_2$), 3.99 (br. s, 2H, NH$_2$), 4.34 (br. s, 2H, NH$_2$), 6.02 (dd, J=2.5, 8.6 Hz, 1H, H-6), 6.21 (d, J=2.6 Hz, 1H, H-2), 6.38 (d, J=8.6 Hz, 1H, H-5). $^{13}$C NMR (125.7 MHz, DMSO d6) δ 28.26 (OC(CH3)3), 39.99 (CH2), 50.82 (CH2), 79.18 (OC(CH$_3$)$_3$), 105.38 (C-2), 106.78 (C-6), 115.65 (C-5), 129.12 (C-4), 136.05 (C-3), 144.06 (C-1), 154.19 (CO). Anal. Calcd for C$_{15}$H$_{24}$N$_4$O$_2$: C, 61.62; H, 8.27; N, 19.16%. Found: C, 61.55; H, 8.31; N, 19.08%.

Example 12

Synthesis of 4-Bromo-1,2-dinitrobenzene 24

To a cold solution of trifluoroacetic acid (25 mL) at 0° C. was added compound 8 (4.96 g, 22.96 mmol). After being stirred for 10 minutes, a solution of 33% hydrogen peroxide (13.75 mL, 133 mmol) was added, and the mixture was stirred at room temperature for 0.5 h, followed by stirring at 50° C. for 2 h. The mixture was poured into ice water, and the solid obtained was filtered and washed with cold water to get the titled compound 24. Yield: 76%, yellow solid. $^1$H NMR (500 MHz, CDCl$_3$) δ 7.85-7.92 (m, 2H, H-5, H-6), 8.04 (br. s, 1H, H-3). $^{13}$C NMR (125.7 MHz, CDCl$_3$) δ 126.39 (C-2), 127.91 (C-3), 128.09 (C-4), 136.29 (C-5), 141.26 (C-1), 143.42 (C-2). Anal. Calcd for C$_6$H$_3$BrN$_2$O$_4$: C, 29.18; 11, 1.22; N, 11.34%. Found: C, 29.12; II, 1.26; N, 11.26%.

Example 13

Synthesis of tert-Butyl 4-(3,4-dinitrophenyl)piperazine-1-carboxylate 25

To an oven-dried flask, 1-boc-piperazine (1.59 g, 8.5 mmol), Cs$_2$CO$_3$ (2.91 g, 8.93 mmol), Pd$_2$(dba)$_3$ (0.72 g, 0.78 mmol), rac-2,2'bis(diphenylphosphino)-1,1'-binaphthyl (0.44 g, 0.71 mmol), toluene (6 mL) and compound 24 (1.76 g, 7.14 mmol) were added. While stirring the reaction mixture at room temperature, the air in the flask was removed and replaced by N$_2$. This process was repeated three times. The reaction mixture was further stirred at room temperature for 0.5 h. Ethyl acetate (50 mL) was added to the mixture at room temperature, washed with H$_2$O (15 mL) and brine (10 mL), dried over Na$_2$SO$_4$, and evaporated. The brown oily material was chromatographed on a silica column, eluting with hexanes:ethyl acetate (30:70), and then changing to (40:60), yielding compound 25. Yield: 78%, yellow solid. IR (KBr, cm$^{-1}$) 3073 (Ar—H), 1683 (CO), 1528, 1432 (C=C), 1226 (C—N), 1151 (C-0); $^1$H NMR (500 MHz, CDCl$_3$) δ 1.48 (9H, s, OC(CH$_3$)$_3$), 3.02 (m, 4H, 2CH$_2$), 3.58 (m, 4H, 2CH$_2$), 7.17 (dd, J=2.6, 8.8 Hz, 1H, H-6), 7.24 (d, J=2.5 Hz, 1H, H-2), 7.71 (d, J=8.5 Hz, 1H, H-4). $^{13}$C NMR (125.7 MHz, CDCl$_3$) δ 28.30 (OC(CH$_3$)$_3$), 48.24 (CH$_2$), 51.39 (CH$_2$), 80.12 (OC (CH$_3$)$_3$), 124.23 (C-2), 124.92 (C-6), 127.49 (C-5), 128.17 (C-4), 141.62 (C-3), 146.94 (C-1), 154.60 (CO). Anal. Calcd for C$_{15}$H$_{20}$N$_4$O$_6$: C, 51.13; 11, 5.72; N, 15.90%. Found: C, 51.07; H, 5.78; N, 15.82%.

Example 14

Synthesis of tert-Butyl 4-(2-oxo-2,3-dihydro-1H-benzo[d]imidazol-5-yl)piperazine-1-carboxylate 20

Following the same procedure adopted for the synthesis of 13, the title compound was obtained by the reaction of compound 23 with CDI. Yield: 66%, colorless solid, nap 250-251° C. IR (KBr, cm$^{-1}$) 3292, 3165 (CONH), 3031 (Ar—H), 2979 (Alph-H), 1692 (CO), 1610, 1509, 1411 (C=C), 1222 (C—N), 1177 (C-0); $^1$H NMR (500 MHz, DMSO d6) δ 1.38 (9H, s, OC(CH$_3$)$_3$), 2.91 (m, 4H, 2CH$_2$), 3.42 (m, 4H, 2CH$_2$),), 6.52 (m, 2H, H-4, H-6), 6.78 (d, J=8.6 Hz, 1H, H-7), 10.42 (br. s, 1H, NH), 10.50 (br. s, 1H, NH). $^{13}$C NMR (125.7 MHz, DMSO d6) δ 28.37 (OC(CH$_3$)$_3$), 40.01 (CH$_2$), 50.66 (CH$_2$), 79.30 (OC(CH$_3$)$_3$), 99.01 (C-4), 109.03 (C-6), 110.55 (C-7), 123.93 (C-8), 130.52 (C-3), 146.58 (C-5), 154.76 (CO), 155.89 (CO). Anal. Calcd for C$_{16}$H$_{22}$N$_4$O$_3$: C, 60.36; H, 6.97; N, 17.60%. Found: C, 60.28; H, 7.03; N, 17.51%.

Example 15

Synthesis of 5-(piperazin-1-yl)-1H-benzo[d]imidazol-2(3H)-one 6

Following the same procedure adopted for the synthesis of 5, the title compound was obtained from the treatment of compound 20 with trifluoroacetic acid. Yield: 93%, light purple solid, mp 110-111° C. IR (KBr, cm$^{-1}$) 3220 (CONH), 3053 (Ar—H), 2936 (Alph-H), 1695 (CO), 1609, 1444 (C=C), 1186 (C—N), 1120 (C-0); $^1$H NMR (500 MHz, DMSO d6) δ 3.19 (m, 4H, 2CH$_2$), 3.22 (m, 4H, 2CH$_2$),), 6.59 (m, 2H, H-4, H-6), 6.80 (d, r=8.8 Hz, 1H, H-7), 8.86 (br. s, 2H, NH), 10.40 (br. s, 1H, NH), 10.53 (br. s, 1H, NH). $^{13}$C NMR (125.7 MHz, DMSO d6) δ 43.10 (CH$_2$), 47.73 (CH$_2$), 98.97 (C-4), 108.84 (C-6), 110.25 (C-7), 124.54 (C-8), 130.57 (C-3), 145.19 (C-5), 155.76 (CO). Anal. Calcd for C$_{13}$H$_{15}$F$_3$N$_4$O$_3$: C, 46.99; H, 4.55; N, 16.86%. Found: C, 46.93; H, 4.60; N, 16.76%.

Example 16

Synthesis of 5-(1-(biphenyl-4-ylmethyl)piperidin-4-yl)-1H-benzo[d]imidazol-2(3H)-one 5a A representative procedure for the synthesis of the piperidinyl aldehydes is the following. To a solution of compound 5 (0.15 g, 0.45 mmol) and biphenyl-4-carbaldehyde a (0.1 g, 0.55 mmol) in DMSO (2 mL) at 0° C. was added Et$_3$N (0.13 mL, 0.97 mmol). After being stirred for 0.5 h at room temperature, NaBH(OAc)$_3$ (0.11 g, 0.53 mmol) was added, and the mixture was stirred for 6 h. To the reaction mixture was added sat. NaHCO$_3$ solution (10 mL), and the mixture was stirred for 15 min, followed by the addition of ethyl acetate (30 mL). The organic layer was separated and washed with sat. NaHCO$_3$ and brine, and dried over Na$_2$SO$_4$ and evaporated. The light yellow solid was crystallized from diethyl ether to obtain the title compound 5a. Yield: 51%, off-white solid, mp>260° C. IR (KBr, cm$^{-1}$) 3429 (CONH), 3055 (Ar—H), 2966 (Alph-H), 1703 (CO), 1620, 1518, 1422 (C=C), 1226 (C—N), 1145 (C-0); $^1$H NMR (500 MHz, DMSO d6) δ 1.62-1.71 (m, 4H, 2CH$_2$), 2.04 (m, 2H, CH$_2$), 2.48 (m, 1H, CH), 2.92 (m, 2H, CH$_2$), 3.51 (s, 2H, NCH$_2$), 6.77-6.81 (m, 3H, 3Ar—H), 7.32 (m, 1H, Ar—H), 7.40-7.45 (m, 4H, 4Ar—H), 7.59-7.64 (m, 4H, 4Ar—H), 10.43 (br. s, 1H, NH), 10.48 (br. s, 1H, NH). $^{13}$C NMR (125.7 MHz, DMSO d6) δ 33.64 (CH$_2$), 41.86 (CH), 53.66 (CH$_2$), 59.45 (NCH$_2$), 106.91 (Ar—C), 108.42 (Ar—C), 118.99 (Ar—C), 126.56 (Ar—C), 126.66 (Ar—C), 127.42 (Ar—C), 127.98 (Ar—C), 129.03 (Ar—C), 129.06 (Ar—C), 129.63 (Ar—C), 138.92 (Ar—C), 140.11 (Ar—C), 155.59 (C=O). Anal. Calcd for C$_{25}$H$_{25}$N$_3$O: C, 78.30; H, 6.57; N, 10.96%. Found: C, 78.22; H, 6.63; N, 10.86%.

Example 17

Synthesis of 5-(14(4'-Fluorobiphenyl-4-yl)methyl) piperidin-4-yl)-1H-benzo[d]imidazol-2(3H)-one 5b Following the same procedure adopted for the synthesis of 5a, the title compound 5b was obtained from the reductive amination of compound 5 and aldehyde b. Yield: 54%, off-white solid, mp>260° C. IR (KBr, cm$^{-1}$) 3419 (CONH), 3045 (Ar—H), 2976 (Alph-H), 1702 (CO), 1622, 1511, 1428 (C—C), 1236 (C—N), 1170 (C-0); $^1$HNMR (500 MHz, DMSO d6) δ 1.66-1.76 (m, 4H, 2CH$_2$), 2.16 (br. s, 2H, CH$_2$), 2.95 (m, 2H, CH$_2$), 3.49 (s, 2H, NCH$_2$), 6.77-6.82 (3H, m, 3Ar—H), 7.25 (m, 2H, 2Ar—H), 7.41 (d, J=7.6 Hz, 2H, 2Ar—H), 7.58 (m, 2H, 2Ar—H), 7.66 (m, 21-1, 2Ar—H), 10.44 (br. s, 1H, NH), 10.49 (br. s, 1H, NH). $^{13}$C NMR (125.7 MHz, DMSO d6) δ 33.22 (CH$_2$), 41.51 (CH), 53.55 (CH$_2$), 61.67 (NCH$_2$), 106.88 (Ar—C), 108.42 (Ar—C), 115.64 (Ar—C), 115.87 (Ar—C), 118.98 (Ar—C), 126.48 (Ar—C), 126.57 (Ar—C), 128.01 (Ar—C), 128.62 (Ar—C), 128.69 (Ar—C), 129.86 (Ar—C), 136.49 (Ar—C), 138.11 (Ar—C), 138.65 (Ar—C), 155.56 (C=O), 160.94 (Ar—C), 162.87 (Ar—C). Anal. Calcd for C$_{25}$H$_{24}$FN$_3$O: C, 74.79; II, 6.03; N, 10.47%. Found: C; C, 74.70; H, 6.07; N, 10.38%.

Example 18

Synthesis of 5-(1-((5-phenylpyridin-3-yl)methyl) piperidin-4-yl)-1H-benzo[d]imidazol-2(3H)-one 5c Following the same procedure adopted for the synthesis of 5a, the title compound 5c was obtained from the reductive amination of compound 5 and aldehyde c. Yield: 46%, off-white solid, mp 236-237° C. IR (KBr, cm$^{-1}$) 3430, 3192 (CONH), 3048 (Ar—H), 2946 (Alph-H), 1693 (CO), 1629, 1516, 1423 (C=C), 1197 (C—N), 1115 (C-0); $^1$H NMR (500 MHz, DMSO d6) δ 1.62-1.70 (m, 4H, 2CH$_2$), 2.08 (m, 2H, CH$_2$), 2.92 (m, 2H, CH$_2$), 3.60 (s, 2H, NCH$_2$), 6.77-6.81 (m, 3H, 3Ar—H), 7.42 (m, 1H, Ar—II), 7.50 (m, 2H, 2Ar—H), 7.71 (m, 2H, 2Ar—H), 7.96 (s, 1H, H-4'), 8.50 (s, 1H, H-2'), 8.76 (s, 1H, H-6'), 10.44 (br. s, 1H, NH), 10.48 (br. s, 1H, NH). $^{13}$C NMR (125.7 MHz, DMSO d6) δ 33.59 (CH$_2$), 41.78 (CH), 53.66 (CH$_2$), 59.45 (NCH$_2$), 106.91 (Ar—C), 108.37 (Ar—C), 118.98 (Ar—C), 126.95 (Ar—C), 127.02 (Ar—C), 127.96 (Ar—C), 128.26 (Ar—C), 129.22 (Ar—C), 129.26 (Ar—C), 134.02 (Ar—C), 134.66 (Ar—C), 138.86 (Ar—C), 146.35 (Ar—C), 149.07 (Ar—C), 155.56 (C=O). Anal. Calcd for C$_{24}$H$_{24}$N$_4$O: C, 74.97; H, 6.19; N, 14.57%. Found: C, 74.89; H, 6.25; N, 14.48%.

Example 19

Synthesis of 5-(1-((5-Fluorophenyl)pyridin-3-yl) methyl)piperidin-4-yl)-1H-benzo[d]imidazol-2(3H)-one 5d Following the same procedure adopted for the synthesis of 5a, the title compound 5d was obtained from the reductive amination of compound 5 and aldehyde d. Yield: 62%, light yellow solid, mp 241-242° C. IR (KBr, cm$^{-1}$) 3410, 3191 (CONH), 3042 (Ar—H), 2956 (Alph-H), 1688 (CO), 1628, 1512, 1430 (C═C), 1170(C—N), 1115 (C-0); $^1$H NMR (500 MHz, DMSO d6) δ 1.59-1.70 (m, 4H, 2CH$_2$), 2.05 (m, 3H, CH, CH$_2$), 2.91 (m, 2H, CH$_2$), 3.58 (s, 2H, NCH$_2$), 6.76-6.81 (m, 3H, 3Ar—H), 7.31 (m, 2H, 2Ar—H), 7.76 (m, 2H, 2Ar—H), 7.77 (s, 1H, H-4'), 8.48 (s, 1H, H-2'), 8.73 (s, 1H, H-6'), 10.43 (br. s, 1H, NH), 10.47 (br. s, 1H, NH). $^{13}$C NMR (125.7 MHz, DMSO d6) δ 33.59 (CH$_2$), 41.79 (CH), 53.68 (CH$_2$), 59.45 (NCH$_2$), 106.91 (Ar—C), 108.38 (Ar—C), 116.02 (Ar—C), 116.21 (Ar—C), 119.0 (Ar—C), 127.98 (Ar—C), 129.07 (Ar—C), 129.13 (Ar—C), 129.20 (Ar—C), 129.84 (Ar—C), 133.57 (Ar—C), 134.02 (Ar—C), 134.33 (Ar—C), 134.64 (Ar—C), 138.87 (Ar—C), 146.28 (Ar—C), 149.07 (Ar—C), 155.59 (C═O). Anal. Calcd for C$_{24}$H$_{23}$FN$_4$O: C, 71.62; H, 5.76; N, 13.92%. Found: C, 71.51; H, 5.83; N, 13.82%.

Example 20

Synthesis of 5-(1-(3-cyclopentenylbenzyl)piperidin-4-yl-1H-benzo[d]imidazol-2(3H)-one 5e Following the same procedure adopted for the synthesis of 5a, the title compound 5e was obtained from the reductive amination of compound 5 and aldehyde e. Yield: 66%, light yellow solid, mp 238-239° C. IR (KBr, cm$^{-1}$) 3322 (CONH), 3051 (Ar—H), 2966 (Alph-H), 1690 (CO), 1636, 1512, 1428 (C═C), 1223 (C—N), 1172 (C-0); $^1$H NMR (500 MHz, DMSO d6) δ 1.59-1.69 (m, 5H, CH, CH$_2$), 1.93 (m, 2H, CH, CH$_2$), 2.04 (m, 2H, CH, CH$_2$), 2.62 (m, 2H, CH, CH$_2$), 2.87 (m, 2H, CH$_2$), 6.24 (s, 1H, CH), 6.76-6.82 (m, 3H, 3Ar—H), 7.16 (m, 1H, Ar—H), 7.24 (m, 1H, Ar—H), 7.30 (m, 1H, Ar—H), 7.38 (m, 1H, Ar—H) 10.44 (br. s, 1H, NH), 10.48 (br. s, 1H, NH). $^{13}$C NMR (125.7 MHz, DMSO d6) δ 22.89 (CH$_2$), 32.83 (CH$_2$), 32.96 (CH$_2$), 33.49 (CH$_2$), 39.00 (CH$_2$), 41.79 (CH), 53.68 (CH$_2$), 62.49 (NCH$_2$), 106.90 (Ar—C), 108.38 (Ar—C), 118.96 (Ar—C), 124.26 (Ar—C), 126.10 (Ar—C), 127.81 (Ar—C), 128.29 (Ar—C), 129.84 (Ar—C), 136.08 (Ar—C), 139.05 (Ar—C), 142.00 (Ar—C), 155.66 (C═O). Anal. Calcd for C$_{24}$H$_{27}$N$_3$O: C, 77.18; H, 7.29; N, 11.25%. Found: C, 77.10; H, 7.36; N, 11.18%.

Example 21

Synthesis of 5-(1-((5-cyclopentenylpyridin-3-yl) methyl)piperidin-4-yl)-1H-benzo[d]imidazol-2(3H)-one 5f Following the same procedure adopted for the synthesis of 5a, the title compound 5f was obtained from the reductive amination of compound 5 and aldehyde f. Yield: 42%, light yellow solid, mp 249-250° C. IR (KBr, cm$^{-1}$) 3342 (CONH), 3040 (Ar—H), 2956 (Alph-H), 1691 (CO), 1634, 1508, 1440 (C═C), 1221 (C—N), 1177 (C-0); $^1$H NMR (500 MHz, DMSO d6) δ 1.601.69 (m, 4H, CH, CH$_2$), 1.95-2.05 (m, 6H, CH, CH$_2$), 2.66 (m, 2H, CH$_2$), 2.85 (m, 2H, CH$_2$), 3.50 (s, 2H, NCH$_2$), 6.41 (s, 1H, CH), 6.76-6.80 (m, 3H, 3Ar—H), 7.73 (s, 1H, H-4'), 8.34 (s, 1H, H-2'), 8.54 (s, 1H, H-6'), 10.43 (br. s, 1H, NH), 10.47 (br. s, 1H, NH). $^{13}$C NMR (125.7 MHz, DMSO-d6) δ 22.77 (CH$_2$), 32.48 (CH$_2$), 33.08 (CH$_2$), 33.55 (CH$_2$), 40.40 (CH$_2$), 41.77 (CH), 53.65 (CH$_2$), 59.51 (NCH$_2$), 106.90 (Ar—C), 108.38 (Ar—C), 118.98 (Ar—C), 127.96 (Ar—C), 128.39 (Ar—C), 129.82 (Ar—C), 131.30 (Ar—C), 133.11 (Ar—C), 133.51 (Ar—C), 138.86 (Ar—C), 139.14 (Ar—C), 145.46 (Ar—C), 148.52 (Ar—C), 155.58 (C═O). Anal. Calcd for C$_{23}$H$_{26}$N$_4$O: C, 73.77; H, 7.00; N, 14.96%. Found: C, 73.69; H, 7.06; N, 14.88%.

Example 22

Synthesis of 5-(4-(biphenyl-4-ylmethyl)piperazin-1-yl)-1H-benzo[d]imidazol-2(3H)-one 6a Following the same procedure adopted for the synthesis of 5a, the title compound 6a was obtained from the reductive amination of compound 6 and aldehyde a. Yield: 46%, off-white solid, mp>260° C. IR (KBr, cm$^{-1}$) 3430 (CONH), 3060 (Ar—H), 2966 (Alph-H), 1705 (CO), 1622, 1511, 1438 (C═C), 1223 (C—N), 1169 (C-0); $^1$H NMR (500 MHz, DMSO d6) δ 2.51 (br. s, 4H, 2CH$_2$), 2.99 (br. s, 4H, 2CH$_2$), 3.53 (s, 2H, NCH$_2$), 6.49 (m, 2H, 2Ar—H), 6.74 (m, 1H, Ar—H), 7.37-7.44 (m, 5H, 5Ar—H), 7.57-7.63 (m, 4H, 4Ar—H), 10.26 (br. s, 1H, NH), 10.38 (br. s, 1H, NH). $^{13}$C NMR (125.7 MHz, DMSO d6) δ 50.13 (CH$_2$), 52.80 (CH$_2$), 61.68 (NCH$_2$), 97.83 (Ar—C), 108.56 (Ar—C), 109.39 (Ar—C), 123.93 (Ar—C), 124.49 (Ar—C), 127.28 (Ar—C), 128.90 (Ar—C), 129.49 (Ar—C), 130.38 (Ar—C), 136.72 (Ar—C), 137.86 (Ar—C), 139.94 (Ar—C), 146.42 (Ar—C), 155.56 (C═O). Anal. Calcd for C$_{24}$H$_{24}$N$_4$O: C, 74.97; H, 6.29; N, 14.57%. Found: C, 74.90; H, 6.35; N, 14.48%.

Example 23

Synthesis of 5-(4-((4-Fluorobiphenyl-4-yl)methyl) piperazin-1-yl)-1H-benzo[d]imidazol-2(3H)-one 6b Following the same procedure adopted for the synthesis of 5a, the title compound 6b was obtained from the reductive amination of compound 6 and aldehyde b. Yield: 55%, off-white solid, mp>260° C. IR (KBr, cm$^{-1}$) 3439 (CONH), 3065 (Ar—H), 2936 (Alph-H), 1707 (CO), 1632, 1501, 1448 (C═C), 1226 (C—N), 1179 (C-0); $^1$H NMR (500 MHz, DMSO d6) δ 2.52 (br. s, 4H, 2CH$_2$), 2.99 (br. s, 4H, 2CH$_2$), 3.53 (s, 2H, NCH$_2$), 6.49 (m, 2H, 2Ar—H), 6.74 (d, J=3.2 Hz, 1H, Ar—H), 7.26 (m, 2H, 2Ar—H), 7.39 (m, 2H, 2Ar—H), 7.58 (m, 2H, 2Ar—H), 7.67 (m, 2H, 2Ar—H), 10.26 (br. s, 1H, NH), 10.37 (br. s, 1H, NH). $^{13}$C NMR (125.7 MHz, DMSO d6) δ 50.13 (CH$_2$), 52.79 (CH$_2$), 61.65 (NCH$_2$), 97.86 (Ar—C), 108.60 (Ar—C), 109.41 (Ar—C), 115.59 (Ar—C), 123.25 (Ar—C), 126.39 (Ar—C), 128.49 (Ar—C), 129.53 (Ar—C), 130.40 (Ar—C), 136.46 (Ar—C), 137.38 (Ar—C), 137.83 (Ar—C), 146.41 (Ar—C), 155.59 (C═O), 160.90 (Ar—C), 162.17 (Ar—C). Anal. Calcd for C$_{24}$H$_{23}$FN$_4$O: C, 71.62; H, 5.76; N, 13.92%. Found: C, 71.55; H, 5.83; N, 13.86.

Example 24

Synthesis of 5-(4-((5-phenylpyridin-3-yl)methyl) piperazin-1-yl)-1,1-benzo[d]imidazol-2(3H)-one 6c Following the same procedure adopted for the synthesis of 5a, the title compound 6c was obtained from the reductive amination of compound 6 and aldehyde c. Yield: 44%, off-white solid, mp 241-242° C. IR (KBr, cm$^{-1}$) 3433, 3195 (CONH), 3038 (Ar—H), 2936 (Alph-H), 1683 (CO), 1639, 1506, 1443 (C═C), 1177 (C—N), 1119 (C-0); $^1$H NMR (500 MHz, DMSO d6) δ 2.51 (br. s, 4H, 2CH$_2$), 2.99 (br. s, 4H, 2CH$_2$), 3.62 (s, 2H, NCH$_2$), 6.50 (m, 2H, 2Ar—H), 6.73 (d, J=3.2 Hz, 1H, Ar—H), 7.41 (m, 1H, Ar—H), 7.47 (m, 2H, 2Ar—H), 7.70 (m, 1H, Ar—H), 7.96 (s, 1H, H-4'), 8.51 (s, 1H, H-2'), 8.77 (s, 1H, H-6'), 10.26 (br. s, 1H, NH), 10.38 (br.

s, 1H, NH). $^{13}$C NMR (125.7 MHz, DMSO-d6) δ 50.11 (CH$_2$), 52.67 (CH$_2$), 59.01 (NCH$_2$), 97.88 (Ar—C), 108.58 (Ar—C), 109.44 (Ar—C), 123.29 (Ar—C), 126.93 (Ar—C), 127.09 (Ar—C), 128.16 (Ar—C), 129.15 (Ar—C), 130.40 (Ar—C), 133.57 (Ar—C), 134.56 (Ar—C), 135.19 (Ar—C), 136.99 (Ar—C), 146.37 (Ar—C), 149.04 (Ar—C), 155.58 (C=O). Anal. Calcd for C$_{23}$H$_{23}$N$_5$O: C, 71.67; H, 6.01; N, 18.17%. Found: C, 71.60; H, 6.06; N, 18.08.

Example 25

Synthesis of 5-(4-((5-(4-fluorophenyl)pyridin-3-yl) methyl)piperazin-1-yl)-1H-benzo[d]imidazol-2(3H)-one 6d Following the same procedure adopted for the synthesis of 5a, the title compound 6d was obtained from the reductive amination of compound 6 and aldehyde d. Yield: 42%, off-white solid, mp 246-247° C. IR (KBr, cm$^{-1}$) 3413, 3190 (CONH), 3048 (Ar—H), 2946 (Alph-H), 1686 (CO), 1629, 1506, 1433 (C=C), 1176 (C—N), 1113 (C-0); $^1$H NMR (500 MHz, DMSO d6) δ 2.52 (br. s, 4H, 2CH$_2$), 2.99 (br. s, 4H, 2CH$_2$), 3.61 (s, 2H, NCH$_2$), 6.50 (m, 2H, 2Ar—H), 6.73 (d, J=3.2 Hz, 1H, Ar—H), 7.31 (m, 2H, 2Ar—H), 7.76 (m, 2H, 2Ar—H), 7.96 (s, 1H, H-4'), 8.50 (s, 1H, H-2'), 8.76 (s, 1H, H-6'), 10.26 (br. s, 1H, NH), 10.38 (br. s, 1H, NH). $^{13}$C NMR (125.7 MHz, DMSO d6) δ 50.08 (CH$_2$), 52.64 (CH$_2$), 58.98 (NCH$_2$), 97.90 (Ar—C), 108.58 (Ar—C), 109.44 (Ar—C), 115.91 (Ar—C), 116.07 (Ar—C), 123.65 (Ar—C), 129.01 (Ar—C), 129.08 (Ar—C), 130.21 (Ar—C), 133.38 (Ar—C), 134.31 (Ar—C), 134.89 (Ar—C), 146.35 (Ar—C), 149.04 (Ar—C), 155.42 (C=O), 161.15 (Ar—C). Anal. Calcd for C$_{23}$H$_{22}$FN$_5$O: C, 68.47; H, 5.50; N, 17.36%. Found: C, 68.46; H, 5.54; N, 17.28%.

Example 26

Synthesis of 5-(4-(3-cyclopentenylbenzyl)piperazin-1-yl)-1H-benzo[d]imidazol-2(3H)-one 6e Following the same procedure adopted for the synthesis of 5a, the title compound 6e was obtained from the reductive amination of compound 6 and aldehyde e. Yield: 62%, off-white solid, mp 244-245° C. IR (KBr, cm$^{-1}$) 3410, 3183 (CONH), 3050 (Ar—H), 2948 (Alph-H), 1689(CO), 1625, 1516, 1430 (C=C), 1178 (C—N), 1115 (C-0); $^1$H NMR (500 MHz, DMSO d6) δ 1.93 (m, 2H, CH$_2$), 2.49 (br. s, 2H, CH$_2$), 2.63 (br. s, 2H, CH$_2$), 2.98 (br. s, 4H, 2CH$_2$), 3.49 (s, 2H, NCH$_2$), 6.24 (br. s, 1H, CH), 6.49 (m, 2H, 2CH), 6.74 (d, J=3.1 Hz, 1H, Ar—H), 7.18 (m, 1H, Ar—H), 7.28 (m, 1H, Ar—H), 7.32 (m, 1H, Ar—H), 7.38 (m, 1H, Ar—H), 10.27 (br. s, 1H, NH), 10.39 (br. s, 1H, NH). $^{13}$C NMR (125.7 MHz, DMSO d6) δ 22.86 (CH$_2$), 32.78 (CH$_2$), 32.94 (CH$_2$), 50.11 (CH$_2$), 52.77 (CH$_2$), 62.08 (NCH$_2$), 97.95 (Ar—C), 108.70 (Ar—C), 109.49 (Ar—C), 124.28 (Ar—C), 126.08 (Ar—C), 127.75 (Ar—C), 128.29 (Ar—C), 130.44 (Ar—C), 136.07 (Ar—C), 141.94 (Ar—C), 146.42 (Ar—C), 155.66 (C—O). Anal. Calcd for C$_{23}$H$_{26}$N$_4$O: C, 73.77; H, 7.00; N, 14.96%. Found: C, 73.68; H, 7.05; N, 14.86%.

Example 27

Synthesis of 5-(4-((5-cyclopentenylpyridin-3-yl) methyl)piperazin-1-yl)-1H-benzo[d]imidazol-2(3H)-one 6f Following the same procedure adopted for the synthesis of 5a, the title compound 6f was obtained from the reductive amination of compound 6 and aldehyde f. Yield: 39%, off-white solid, mp 255-256° C. IR (KBr, cm$^{-1}$) 3332 (CONH), 3030 (Ar—H), 2951 (Alph-H), 1689 (CO), 1644, 1506, 1450 (C=C), 1222 (C—N), 1176 (C—O); $^1$H NMR (500 MHz, DMSO d6) δ 1.95 (m, 2H, CH$_2$), 2.51 (br. s, 2H, CH$_2$), 2.66 (m, 2H, CH$_2$), 2.98 (br. s, 4H, 2CH$_2$), 3.54 (m, 2H, NCH$_2$), 6.42 (br. s, 1H, CH), 6.50 (m, 2H, 2Ar—H), 6.74 (m, 1H, Ar—H), 7.74 (s, 1H, H-4'), 8.36 (s, 1H, H-2'), 8.57 (s, 1H, H-6'), 10.26 (br. s, 1H, NH), 10.40 (br. s, 1H, NH). $^{13}$C NMR (125.7 MHz, DMSO d6) δ 22.69 (CH$_2$), 32.40 (CH$_2$), 33.01 (CH$_2$), 50.06 (CH$_2$), 52.66 (CH$_2$), 59.06 (NCH$_2$), 97.92 (Ar—C), 108.61 (Ar—C), 109.46 (Ar—C), 123.31 (Ar—C), 128.31 (Ar—C), 130.40 (Ar—C), 131.21 (Ar—C), 133.04 (Ar—C), 139.03 (Ar—C), 145.56 (Ar—C), 146.37 (Ar—C), 148.52 (Ar—C), 155.61 (C=O). Anal. Calcd for C$_{22}$H$_{25}$N$_5$O: C, 70.38; H, 6.71; N, 18.65%. Found: C, 70.30; H, 6.75; N, 18.55%.

It is to be understood that the present invention is not limited to the embodiments described above, but encompasses any and all embodiments within the scope of the following claims.

I claim:

1. A benzo[d]imidazole derivative of piperidine or piperazine, of the formula:

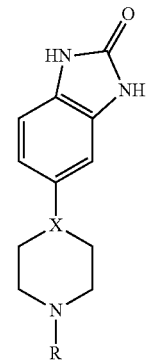

wherein X is carbon or nitrogen and R is a group selected from a, b, c, d, e, and f selected from the group consisting of:

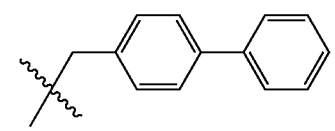

a

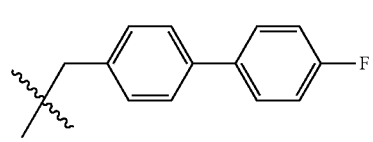

b

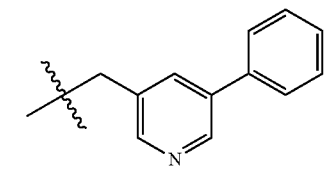

c

-continued

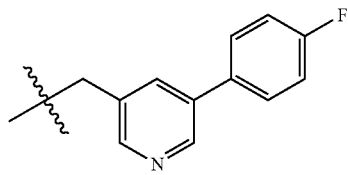
d

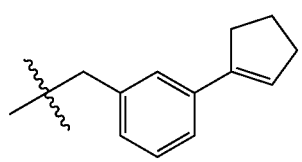
e and

f or a pharmaceutically acceptable salt thereof.

2. The benzo[d]imidazole derivative of piperidine or piperazine according to claim 1, wherein X is carbon and R is group a.

3. The benzo[d]imidazole derivative of piperidine or piperazine according to claim 1, wherein X is carbon and R is group b.

4. The benzo[d]imidazole derivative of piperidine or piperazine according to claim 1, wherein X is carbon and R is group c.

5. The benzo[d]imidazole derivative of piperidine or piperazine according to claim 1, wherein X is carbon and R is group d.

6. The benzo[d]imidazole derivative of piperidine or piperazine according to claim 1, wherein X is carbon and R is group e.

7. The benzo[d]imidazole derivative of piperidine or piperazine according to claim 1, wherein X is carbon and R is group f.

8. The benzo[d]imidazole derivative of piperidine or piperazine according to claim 1, wherein X is nitrogen and R is group a.

9. The benzo[d]imidazole derivative of piperidine or piperazine according to claim 1, wherein X is nitrogen and R is group b.

10. The benzo[d]imidazole derivative of piperidine or piperazine according to claim 1, wherein X is nitrogen and R is group c.

11. The benzo[d]imidazole derivative of piperidine or piperazine according to claim 1, wherein X is nitrogen and R is group d.

12. The benzo[d]imidazole derivative of piperidine or piperazine according to claim 1, wherein X is nitrogen and R is group e.

13. The benzo[d]imidazole derivative of piperidine or piperazine according to claim 1, wherein X is nitrogen and R is group f.

14. A method of making a benzo[d]imidazole derivative of piperidine, comprising the steps of:
removing the Boc group from tert-Butyl-4-(2-oxo-2,3-dihydro-1H-benzo[d]imidazol-5-yl)piperidine-1-carboxylate to form 5-(piperidin-4-yl)-1H-benzo[d]imidazol-2(3H)-one; and
reductively aminating the 5-(piperidin-4-yl)-1H-benzo[d]imidazol-2(3H)-one with a biarylaldehyde having a functional group selected from group a, b, c, d, e, and f selected from the group consisting of:

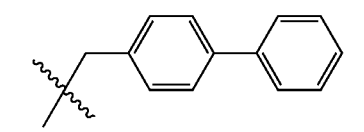
a

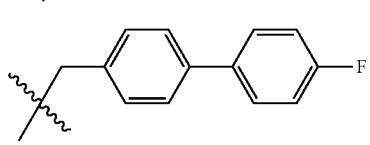
b

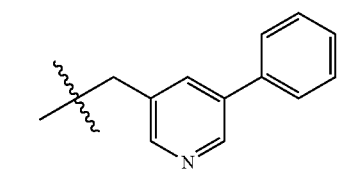
c

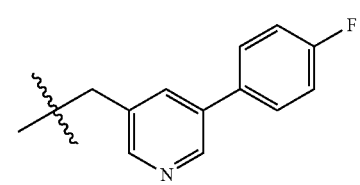
d

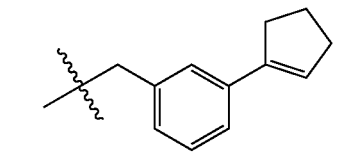
e and

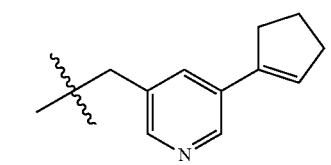
f

* * * * *